(12) United States Patent
Nakhjavani et al.

(10) Patent No.: US 10,466,187 B2
(45) Date of Patent: Nov. 5, 2019

(54) OPTIMIZATION AND INTEGRATION OF THERMAL AND STRUCTURAL ANALYSES

(71) Applicant: The Boeing Company, Chicago, IL (US)

(72) Inventors: Omid B. Nakhjavani, Kirkland, WA (US); Mohammad Ali Heidari, Bellevue, WA (US); Milan Stefanovic, Everett, WA (US); Bradley A. Olmstead, Enumclaw, WA (US); Eric John Zimney, North Charleston, SC (US); Naveena Mallikarjunaiah, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 885 days.

(21) Appl. No.: 14/735,751

(22) Filed: Jun. 10, 2015

(65) Prior Publication Data

US 2016/0363546 A1 Dec. 15, 2016

(51) Int. Cl.
*G01N 25/00* (2006.01)
*G06F 17/50* (2006.01)

(52) U.S. Cl.
CPC ......... *G01N 25/00* (2013.01); *G06F 17/5018* (2013.01); *G06F 17/5095* (2013.01); *G06F 2217/80* (2013.01)

(58) Field of Classification Search
None
See application file for complete search history.

(56) References Cited

U.S. PATENT DOCUMENTS

| 8,725,470 | B1 * | 5/2014 | Brown | G06F 17/5009 |
| | | | | 703/2 |
| 2002/0177985 | A1 * | 11/2002 | Kraft | G06F 17/50 |
| | | | | 703/7 |

(Continued)

OTHER PUBLICATIONS

Bannerjee, Dilip K., "Software Independent Data Mapping Tool for Structural Fire Analysis," NIST Technical Note 1828, Feb. 2014, 45 pages.*

(Continued)

*Primary Examiner* — Alexander Satanovsky
*Assistant Examiner* — Brent A. Fairbanks
(74) *Attorney, Agent, or Firm* — Hanley, Flight & Zimmerman, LLC

(57) ABSTRACT

Example systems and methods to optimize and integrate of thermal and structural analyses are described herein. An example method includes performing a thermal analysis of a component using a first mesh representing the component to produce a thermal distribution across the component. The first mesh has first nodes based on a first element size. The example method includes using a first mapping file to assign temperature values to second nodes of a second mesh representing the component based on the thermal distribution. The second nodes are based on a second element size different than the first element size. The example method also includes performing a structural analysis of the component using the second mesh and the assigned temperature values to produce gauge sizes for the component and using a second mapping file to assign gauge values to the first nodes of the first mesh based on the gauge sizes.

17 Claims, 10 Drawing Sheets

(56) References Cited

U.S. PATENT DOCUMENTS

2003/0204823 A1* 10/2003 Armstrong .............. G06F 17/50
                                                        703/1
2012/0016639 A1*  1/2012 Duan ................. G06F 17/5018
                                                        703/1
2016/0125107 A1*  5/2016 Druckman .......... G06F 17/5018
                                                        703/2

OTHER PUBLICATIONS

Bannerjee, Dilip K., "Software Independent Data Mapping Tool for Structural Fire Analysis," NIST Technical Note 1828, Feb. 2014, 45 pages. (Year: 2014).*

European Patent Office, "Extended European Search Report," issued in connection with European Patent Application No. 16170095.0, dated Nov. 15, 2016, 9 pages.

Geis et al., "Collaborative design and analysis of electro-Optical sensors," Optical Modeling and Performance Predictions IV, SPIE vol. 7427, Oct. 2, 2009, 12 pages.

Panczak et al., "Integrating Thermal and Structural Analysis with Thermal Desktop (TM)," Jan. 1, 1999, Society of Automotive Engineers, Inc., Retrieved from the Internet: https://www.crtech.com/sites/default/files/publications/99es-40.pdf on Nov. 2, 2016, 7 pages.

* cited by examiner

OPTIMIZATION AND INTEGRATION OF THERMAL AND STRUCTURAL ANALYSES

FIELD OF THE DISCLOSURE

This disclosure relates generally to thermal and structural analyses and, more particularly, to the optimization and integration of thermal and structural analyses.

BACKGROUND

Thermal and structural analyses are often performed on components, such as aircraft parts, using finite element analysis of a model of the component. Finite element analysis involves approximating solutions across a plurality of elements or nodes that form a mesh. A thermal analysis is performed by a thermal program or software that analyzes a thermal mesh representing the component and produces thermal distribution information across the nodes of the thermal mesh. A structural analysis is performed by a structural program or software that analyzes a structural mesh representing the component to produce structural information, such as optimal gauge sizes, across the nodes of the structural mesh. In general, the thermal analysis is typically more complex and requires more time to complete. As such, the thermal mesh is generally coarser or has larger elements or node spacings than the structural mesh. To optimize the design of the component, the thermal distribution information is needed for the structural analysis and the gauge sizes are needed for the thermal analysis. However, because the thermal and structural meshes are different, the nodes of these meshes do not align. As a result, the information from the nodes of one mesh cannot be correlated directly with the nodes of the other mesh. In current practice, technicians attempt to manually associate the information from each of the nodes of one mesh to the nodes of the other mesh, on a node-by-node basis.

SUMMARY

An example method disclosed herein includes performing a thermal analysis of a component using a first mesh representing the component to produce a thermal distribution across the component. The first mesh has first nodes based on a first element size. The example method includes using a first mapping file to assign temperature values to second nodes of a second mesh representing the component based on the thermal distribution. The second nodes are based on a second element size different than the first element size. The example method also includes performing a structural analysis of the component using the second mesh and the assigned temperature values to produce gauge sizes for the component and using a second mapping file to assign gauge values to the first nodes of the first mesh based on the gauge sizes.

An example apparatus disclosed herein includes a thermal analyzer to perform a thermal analysis of a component using a first mesh representing the component to produce a thermal distribution across the component. The first mesh has first nodes based on a first element size. The example apparatus includes a first mapper to assign temperature values to second nodes of a second mesh representing the component. The second nodes are based on a second element size different than the first element size. The example apparatus also includes a structural analyzer to perform a structural analysis using the second mesh to produce gauge sizes for the component and a second mapper to assign gauge values to the first nodes of the first mesh based on the gauge sizes.

A tangible computer readable storage medium is disclosed herein that includes instructions that, when executed, cause a machine to at least generate a first mesh representing a component, where the first mesh has first nodes, and generate a second mesh representing the component, where the second mesh has second nodes. A portion of the second nodes correspond to different coordinates of the component than the first nodes. The instructions also cause the machine to perform a thermal analysis of the component using the first mesh to produce a thermal distribution across the component and assign, via a first mapping file, temperature values to the second nodes based on the thermal distribution. The instructions also cause the machine to perform a structural analysis on the second mesh to produce gauge sizes for the component and assign, via a second mapping file, gauge values to the first nodes of the first mesh based the on the gauge sizes.

Figure 1:
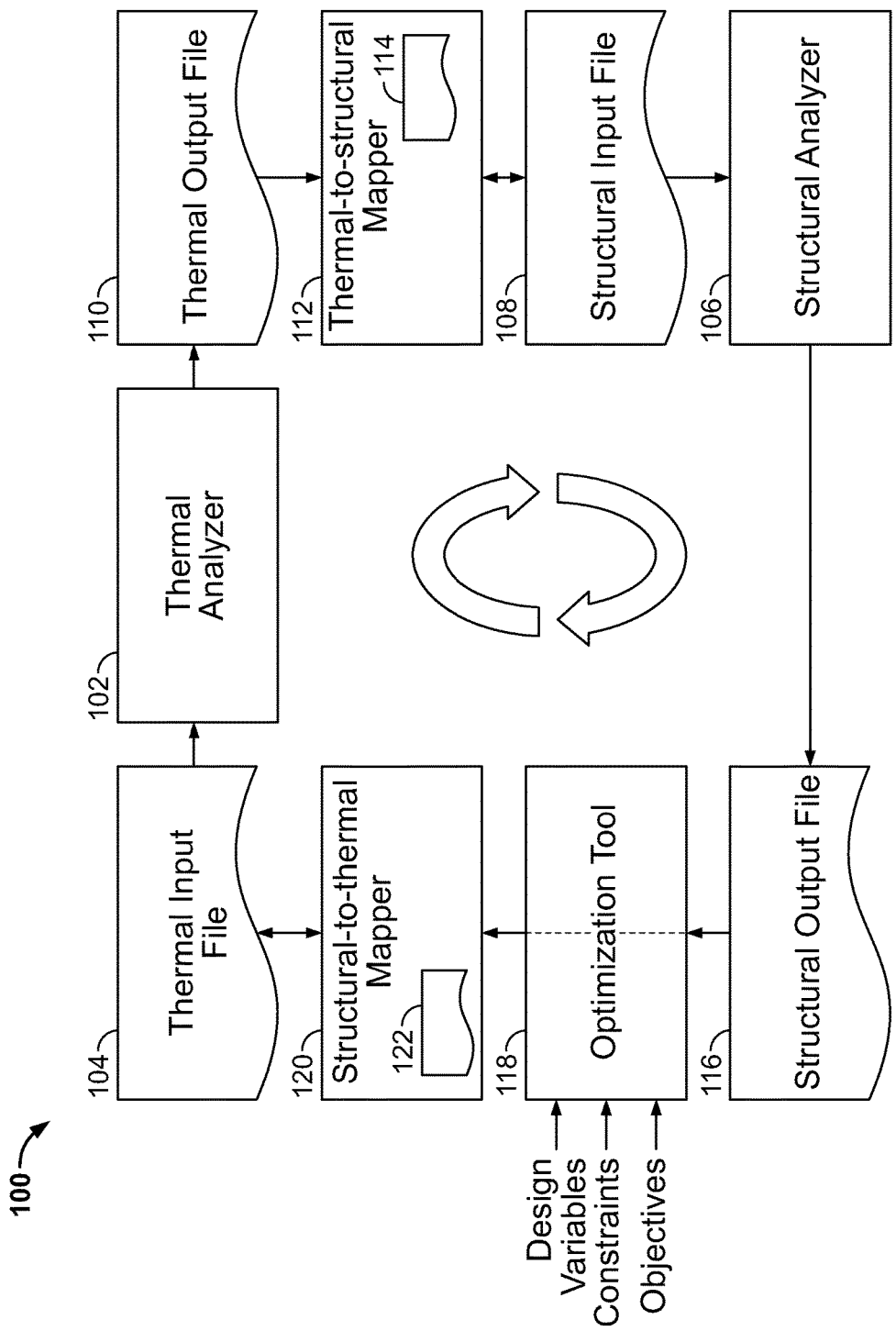
FIG. 1 is a block diagram of an example system having an example thermal-to-structural mapper and an example structural-to-thermal mapper to optimize thermal and structural analyses of a component in accordance with the teachings of this discourse.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

DETAILED DESCRIPTION

Components, such as aircraft parts, are typically studied and analyzed to ensure structural and thermal integrity. A thermal analysis, for example, may be performed to determine the temperatures that might be experienced across a given component and whether such temperatures can be withstood. A structural analysis, for example, may be performed to determine optimum thicknesses or gauges across the component to ensure structural integrity of the component. These two analyses (e.g., disciplines) are performed separately though, and integration of these two analyses is not feasible because of complexity and run time for each analysis. Thus, the optimization process typically requires a long time to complete.

Thermal and structural analyses often use a finite element analysis or finite element method (FEM). Finite element analysis involves approximating solutions across a plurality of elements or nodes, which form a mesh. Thermal and structural analyses use different size meshes in the FEM. However, to optimize design variables or constraints of a component (e.g., the gauges, the material type, etc.), the thermal distribution information is needed for the structural analysis and the structural information is needed for the thermal analysis.

In known systems, the thermal analysis is performed first with initial or approximate gauge sizes. The thermal analysis produces thermal distribution information (e.g., temperature gradients) across the nodes of the thermal mesh. After the thermal analysis is completed, the structural analysis is performed using the thermal distribution information. In other words, temperature values are to be assigned to each of the nodes of the structural mesh provided by the thermal analysis. However, because the thermal and structural meshes are different, the nodes of these meshes do not align. In current practice, the nodal temperatures are manually determined for each of the nodes of the structural mesh, which often takes a significant amount of time (e.g., weeks). Once the nodes of the structural mesh have been updated with the thermal distribution information, the structural analysis is then performed on the structural mesh and the optimized gauge sizes are produced. However, the gauge sizes are often different than the initial gauge sizes used in the thermal analysis. Therefore, the thermal analysis may have to be performed again, with the updated gauge sizes. As such, the gauge sizes produced by the structural analysis are manually correlated to the nodes of the thermal mesh so that the thermal analysis can be performed again. However, as mentioned above, the nodes of the structural and thermal meshes do not align. Therefore, the gauge sizes are manually determined for each of the nodes of the thermal mesh, which likewise requires a significant amount of time. If the thermal constraints are violated (e.g., the component may fail due to excessive heat), the thermal distribution information may again need to be correlated back to the structural mesh so the structural analysis can be performed again. This process is tedious but necessary to ensure the component meets or satisfies the structural and thermal requirements.

The systems and methods disclosed herein utilize mapping techniques that correlate information from thermal mesh nodes to structural mesh nodes and from structural mesh nodes to thermal mesh nodes. As a result, the thermal distribution information produced by a thermal analysis can be quickly transferred to the nodes of the structural mesh so that a structural analysis can be performed on the structural mesh with the thermal distribution information. Additionally, the structural distribution information, such as the gauge sizes or thicknesses, produced by the structural analysis can be quickly transferred to the nodes of the thermal mesh. In this manner, the thermal analysis can be performed to ensure the thermal constraints have not been violated. As a result, multiple iterations of this cycle can be performed relatively quickly, thereby enabling the system to optimize the design variables of the component in less time.

An example technique is disclosed herein for mapping thermal distribution information to the nodes of a structural mesh. The example technique includes determining a location of a node in the structural mesh and creating a reference point at the same location in a thermal distribution map and/or a thermal mesh. The technique then determines a thermal distribution value at the reference point and associates the value with the node of the structural mesh. This process may be performed for each node so that correct thermal distribution values can be used at each node of the structural mesh. In some examples, a mapping file is created so that temperature values can be assigned to the nodes of the structural mesh.

Another example technique is disclosed herein for mapping structural distribution information, such as gauge sizes, to nodes of a thermal mesh. The example mapping technique includes identifying a zone of a component that has a consistent gauge size throughout. A reference point is created in the middle of the zone, the closest node to the reference point is identified and the gauge size for the node is extracted. In the thermal mesh, a corresponding reference point is created in the same zone and the closest node to the reference points is identified. The closest node can then be identified as having the gauge size of the reference point. All of the nodes of the thermal mesh falling in the zone can then be identified and updated with the gauge size. This process may be performed for multiple zones of the component. In some examples, a mapping file is created so that the gauge sizes determined by the structural analysis can be assigned to the nodes of the thermal mesh.

Multiple iterations of the thermal and structural analyses can be performed until the design variables (e.g., gauge sizes, material type, etc.) converge and satisfy the constraints (e.g., structural margins, fatigue, thermal limitations, boundaries, etc.). The final solution is an optimum design that satisfies both analyses and achieves a design objective (e.g., minimum weight). Considerations such as cost, weight and scheduling can all be improved using the example systems and methods disclosed herein.

FIG. 1 illustrates an example thermal-structural optimization system 100 that may be used to perform thermal and structural analyses to optimize a design of a component. The example system 100 includes a thermal analyzer 102 that performs a thermal analysis of the component using a thermal mesh that represents the component. The thermal mesh includes a plurality of nodes based on an element size. The thermal mesh is included in a thermal input file 104, which may include additional information (e.g., one or more inputs or constraints) such as the sizes and dimensions of the component (e.g., the gauges at the nodes), the type of material, the location of certain stresses, initial nodal temperatures, etc. The thermal analyzer 102 performs a finite element analysis (e.g., or FEM) on the thermal mesh and produces thermal distribution information, such as nodal temperatures across thermal mesh. The thermal analysis may determine if one or more thermal constraints (e.g., the temperate of the component should not exceed a threshold temperature) have been violated. In the illustrated example, the thermal analyzer 102 may be implemented by any computer program or software such as, for example, Sinda Thermal Analyzer, manufactured by MSC Software Corporation of Newport Beach, California.

The example system 100 also includes a structural analyzer 106 that performs a structural analysis on the component using a structural mesh representing the component. The structural mesh, like the thermal mesh, has a plurality of nodes based on an element size. The structural mesh is included in a structural input file 108, which may include additional information (e.g., one or more inputs or constraints) such as the dimensions of the component, the type of material, temperatures, etc. Using FEM, the structural analyzer 106 analyzes the component, via the structural mesh, and determines optimal gauge sizes (e.g., thicknesses) for the component (e.g., across a plurality of nodes of the structural mesh). In the illustrated example, the structural analyzer 106 may be implemented by any computer program or software such as, for example, Altair® OptiStrcut®, manufactured by Altair Hyperworks of Troy, Mich.

Figure 2:
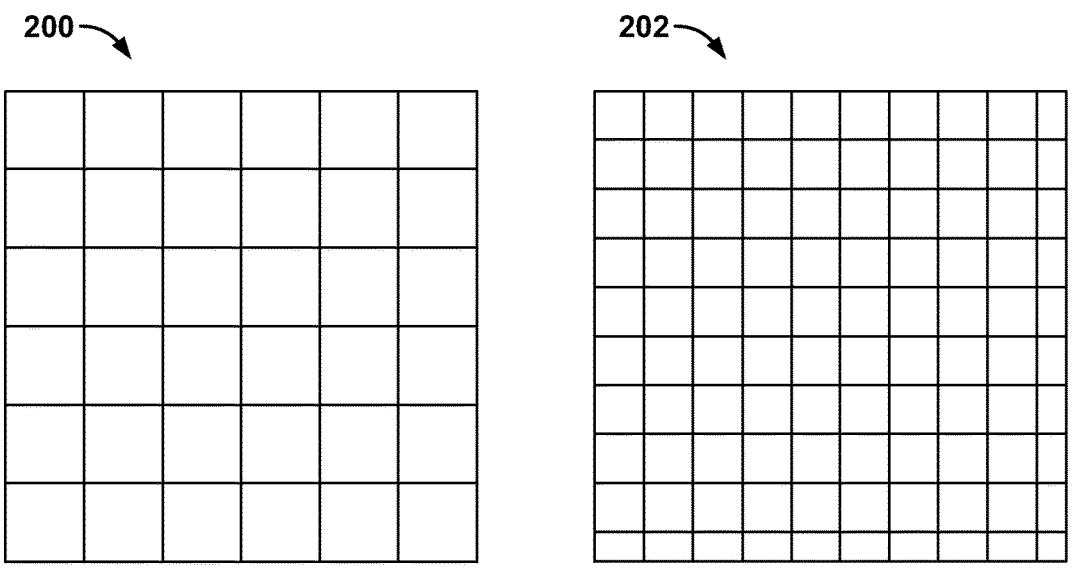
FIG. 2 shows an example thermal mesh that may used for an example thermal analysis by the example system of FIG. 1 and an example structural mesh that may be used for an example structural analysis by the example system of FIG. 1.

To perform the thermal analysis, the gauge sizes or dimensions (e.g., the thicknesses of the sections) of the component are needed, and to perform the structural analysis, temperature values across the component are needed. However, the nodes of structural mesh and the nodes of thermal mesh do not align. In particular, the thermal mesh is typically coarser with larger element sizes (e.g., the nodes are further apart), whereas the structural mesh is finer with relatively smaller element sizes (e.g., the nodes are closer together). FIG. 2 illustrates an example of a thermal mesh 200 representing a component and a structural mesh 202 representing the same component. As shown, using a global coordinate system (e.g., starting from the bottom left corner in each mesh 200, 202), the locations of the nodes (e.g., the intersection of any two lines) of the thermal mesh 200 do not align with the location of the nodes in the structural mesh 202, and vice versa. In order to perform the structural analysis, the thermal distribution information (e.g., the nodal temperatures of the thermal mesh) needs to be associated with or assigned to the nodes in the structural mesh. Likewise, in order to perform the thermal analysis, the gauge sizes at the nodes of the structural mesh need to be associated with or assigned to the nodes in the thermal mesh. However, because the nodes of each do not align, current systems require an operator to manually determine which values should be assigned to which nodes.

Referring to FIG. 1, the thermal optimization analyzer 102 generates a thermal output file 110 with thermal distribution information (e.g., thermal margin information) of the component. The thermal output file 110 may be one file or multiple files that include information about the results of the thermal analysis. For example, the thermal distribution information may include thermal boundaries or temperatures that may be experienced across the component, the locations of the boundaries, the locations of the nodes of the thermal mesh, the temperatures at the nodes, the temperatures at each node with respect to time, etc. In some examples, the thermal output file 104 is a text file (e.g., in txt.outfile format).

Figure 3:
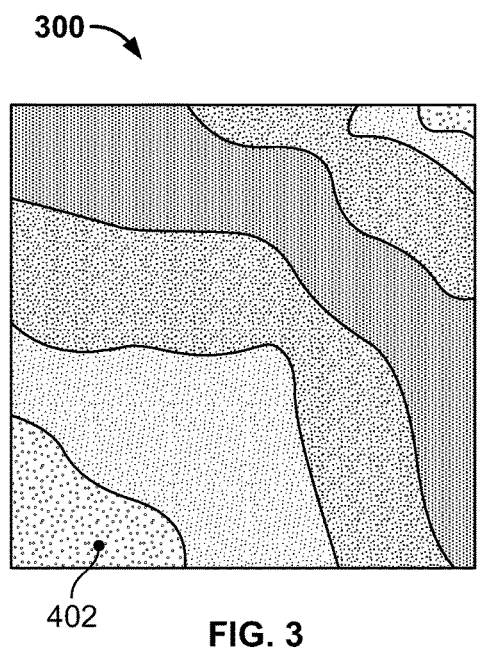
FIG. 3 shows an example thermal distribution map produced by an example thermal analysis using the example system of FIG. 1.
Figure 4:
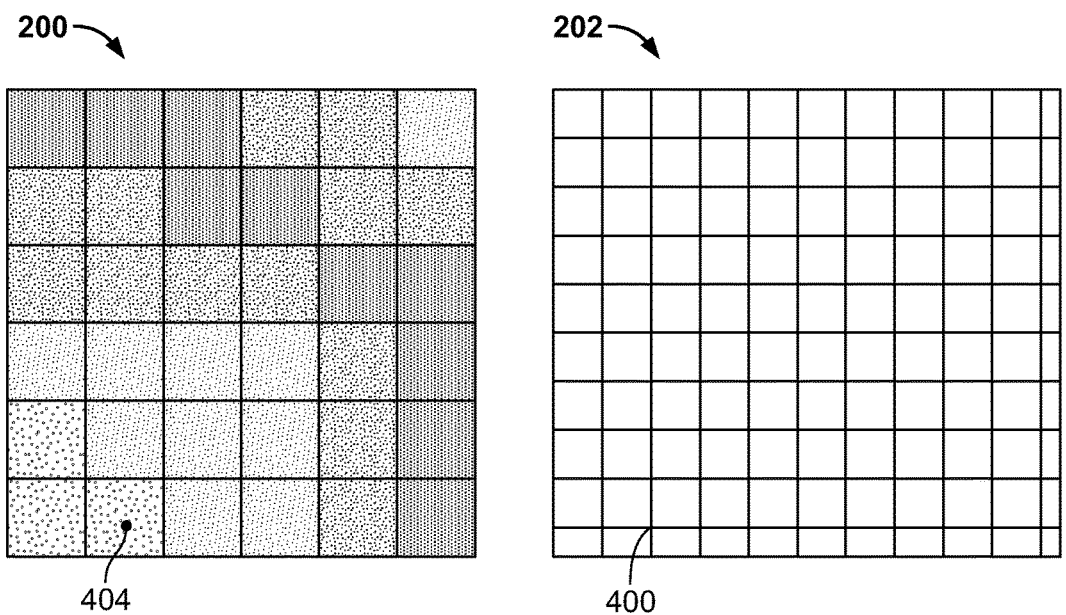
FIG. 4 shows an example mapping technique used to associate thermal distribution information from the example thermal distribution map of FIG. 3 and/or from the example thermal mesh of FIG. 2 to a node of the example structural mesh of FIG. 2.

FIG. 3 shows an example thermal distribution map 300 that may be generated by the thermal analyzer 102. The example thermal distribution map 300 shows the temperature distribution or gradient that may be experienced across the component. The shading and boundary lines in the thermal distribution 300 are for illustrative purposes only. Additionally or alternatively, FIG. 4 shows the thermal distribution information as corresponding to the nodes of thermal mesh 200. As illustrated, the element size of the thermal mesh 200 (e.g., the spacing between the nodes) is relatively large. A such, the granularity or fidelity of the thermal distribution across the nodes is of lower quality. The structural mesh 202 has a smaller element size and, therefore, one or more nodes of the structural mesh 202 may fit within an element of the thermal mesh 200 (e.g., between the nodes of the thermal mesh 200). As such, the temperatures at the nodes of the thermal mesh 200 cannot be directly correlated or mapped to the nodes of the structural mesh 202, because the temperatures boundaries within the elements are not accounted for in the thermal mesh 200. For example, using a global coordinate system, the location of a node 400 in the structural mesh 202 does not align with a node in the thermal mesh 200, as illustrated in FIG. 4.

Figure 5:
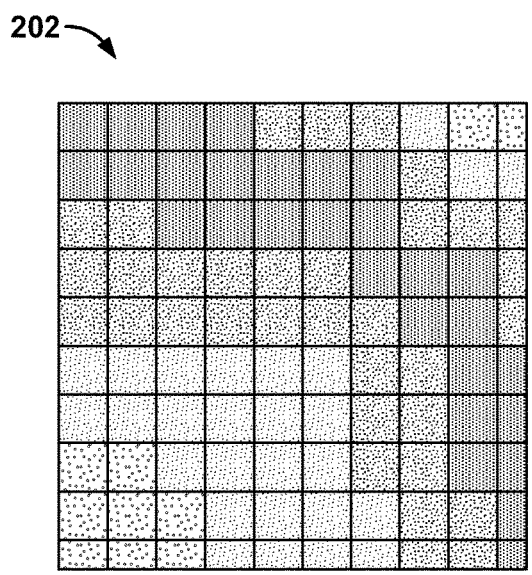
FIG. 5 shows an example result of the example structural mesh of FIG. 2 with the thermal distribution information after the example mapping technique of FIG. 4.

To map or associate the thermal distribution information to the nodes of the structural mesh 202, the example system 100 of FIG. 1 includes a thermal-to-structural mapper 112. The thermal-to-structural mapper 112 determines the temperature information that should be associated with or assigned to each of the nodes of the structural mesh 202 to update the structural input file 108. For example, the thermal-to-structural mapper 112 may determine a location (e.g., a three-dimensional coordinate, (X, Y, Z)) of the node 400, using a global coordinate system, and create a temporary or reference point 402 (e.g., a dummy point) in the thermal distribution map 300 at the same location, as illustrated in FIG. 3. The thermal-to-structural mapper 112 determines the temperature at the reference point 402 and assigns the temperature to the node 400 in the structural mesh 202. In the illustrated example, the thermal-to-structural mapper 112 generates or creates a file 114 that maps the location of the reference point 402 (and the corresponding temperature) from the thermal distribution map 300 to the node 400 of the structural mesh 202 of the structural input file 108. This operation may be performed for each node of the structural mesh 202. In some examples, file 114 includes mappings for all of the nodes of the structural mesh 202. In other examples, the file 114 includes mappings for a batch (e.g., a portion) of the nodes of the structural mesh 202. In some examples, the file 114 is a Tool Command Language (TCL) scripting file or TCL/tk scripting file. The file 114 is used to input the temperatures to the nodes of the structural mesh 202 of the structural input file 108. FIG. 5 illustrates an example of the structural mesh 202 showing the thermal distribution information. The structural mesh 202, including the nodal temperatures, can then be analyzed by the structural analyzer 106.

Additionally or alternatively, a reference point 404 may be created in the thermal mesh 200 of the thermal output file 110 at the same location as the location of the node 400 of the structural mesh 202. A temperature value may be estimated for the reference point 404 by integrating the thermal distribution in the thermal mesh 200 with respect to scaling criteria. In some examples, the temperature value at the reference point 404 is determined based on a gradient (e.g., using an integral) between two or more of the nodes of the thermal mesh 200. For example, the thermal-to-structural mapper 112 may integrate (e.g., via an interpolation process) the temperature values between two or more of the nodes near the reference point 404 to determine a temperature distribution between the two or more nodes, which can be used to determine a temperature value at the reference point 404 (e.g., and, thus, the temperature at the node 400 of the structural mesh 202). In such an example, the file 114 may map the location of the reference point(s) (and the corresponding estimated temperature values) in the thermal mesh 200 of the thermal output file 110 to the nodes of the structural mesh 202 of the structural input file 108.

With the thermal distribution information inputted for each of the nodes of the structural mesh 202, the structural analyzer 106 performs a finite element analysis on the structural mesh 202 to determine optimal gauge sizes or thicknesses for the component and/or to determine if any structural constraints have been violated (e.g., the component may fail at a certain point unless the thickness is increased). The structural analyzer 106 produces a structural output file 116 (e.g., a .out file) that includes optimal gauge sizes for the component, which may be represented by the gauge sizes at the nodes the structural mesh 202. The results of the structural analysis and/or the thermal analysis (e.g., the optimal gauges and/or thermal distribution information) are monitored by an optimization tool 118, disclosed in further detail here.

In some examples, to verify the gauge sizes produced by the structural analyzer 106 conform with the temperature constraints, the component is to be reanalyzed by the thermal analyzer 102 with the updated gauges. In other words, the thermal analysis of the thermal mesh 200 is to be performed a subsequent time using the updated gauge sizes from the structural output file 116. However, as previously explained, the nodes of the structural mesh 202 do not align with the nodes of the thermal mesh 200. Therefore, the optimal gauge sizes at the nodes of the structural mesh 202 cannot be mapped directly to the nodes of the thermal mesh 200.

Figure 6:
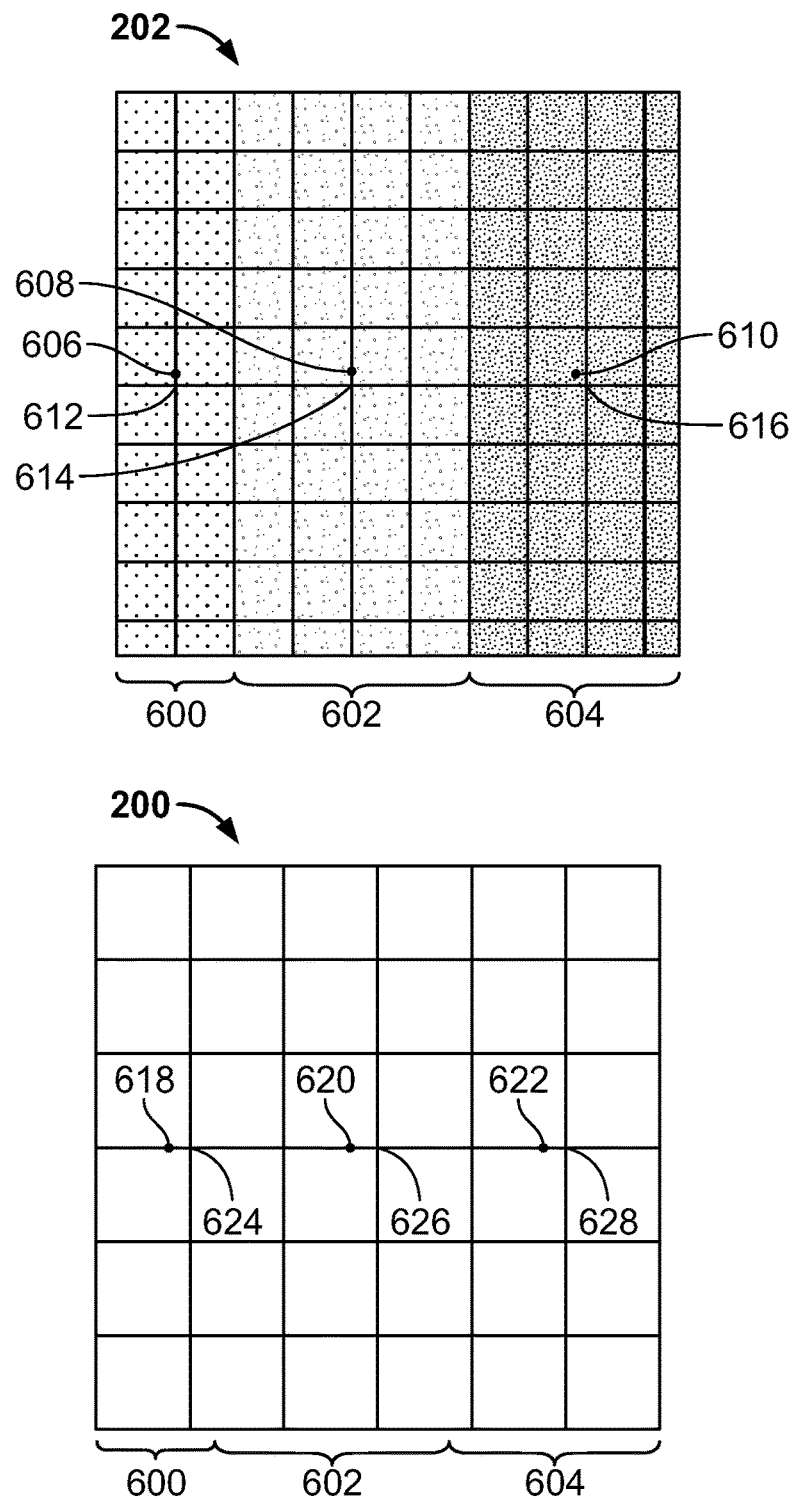
FIG. 6 shows an example mapping technique used to associate structural information, such as gauge sizes, from the example structural mesh of FIG. 2 to nodes of the example thermal mesh of FIG. 2.

To map or associate the structural information to the nodes of the thermal mesh 200, the example system 100 includes a structural-to-thermal mapper 120. The structural-to-thermal mapper 120 determines the gauge sizes to be associated with or assigned to the nodes of the thermal mesh 200 to update the thermal input file 104. For example, the component may be divided (e.g., segmented, partitioned, defined) into zones, where each zone has a constant or consistent gauge size throughout the respective zone. Turning to FIG. 6, a first zone 600, a second zone 602 and a third zone 604 of the component are depicted in the structural mesh 202. In the illustrated example, each of the zones 600, 602, 604 has been shaded to enhance clarity. In the illustrated example, the zones 600, 602, 604 form columns or rectangular sections. However, in other examples, the zones may take any shape. Each of the nodes of the structural mesh 202 in the first zone 600 have the same gauge, each of the nodes of the structural mesh 202 in the second zone 602 have the same gauge, and each of the nodes of the structural mesh 202 in the third zone 604 have the same gauge. There may be more or fewer zones depending on the component and the constraints of the analysis. The boundaries or coordinates of the zones 600, 602, 604 and/or the nodes that fall within each of the zones 600, 602, 604 of the structural mesh 202 are known. For example, the nodes of the structural mesh 202 that are located in the first zone 600 may all include the same property name, e.g., PSHELL1, which refers to a first gauge, the nodes of the structural mesh 202 that are located in the second zone 602 may all include the same property name, e.g., PSHELL2, which refers to a second gauge, and the nodes of the structural mesh 202 that are located in the third zone 604 may all include the same property name, e.g., PSHELL3, which refers to a third gauge. Similar to the structural mesh 202, the nodes of the thermal mesh 200 may include property names that refer to specific gauges. For example, the nodes of the thermal mesh 200 that are located in the first zone 600 may all include the same property name, e.g., GAUGE1, which refers to a first gauge, the nodes of the thermal mesh 200 that are located in the second zone 602 may all include the same property name, e.g., GAUGE2, which refers to a second gauge, and the nodes of the thermal mesh 200 that are located in the third zone 604 may all include the same property name, e.g., GAUGE3, which refers to a third gauge. The structural-to-thermal mapper 120 generates or creates a file 122 that maps the gauge sizes associated with the property names of the structural output file 116 to the gauge sizes associated with the property names of the thermal input file 104.

For example, to map the gauges from the zones 600, 602, 604 of the structural mesh 202 to the nodes in the thermal mesh 200, the structural-to-thermal mapper 120 may create or define a reference point for each of the zones 600, 602, 604, which can then be used to correlate the gauge sizes in the zones 600, 602, 604 of the structural mesh 202 to the nodes of the thermal mesh 200 that are located within the respective zones 600, 602, 604. The locations of the reference points are based on a global coordinate system that can be used in both the thermal mesh 200 and the structural mesh 202. In some examples, the reference points are located at the centers of the respective zones 600, 602, 604. The structural-to-thermal mapper 120 creates a file, such as a comma-separated values (CSV) file 122, with the coordinates or locations of the reference points.

Figure 7:
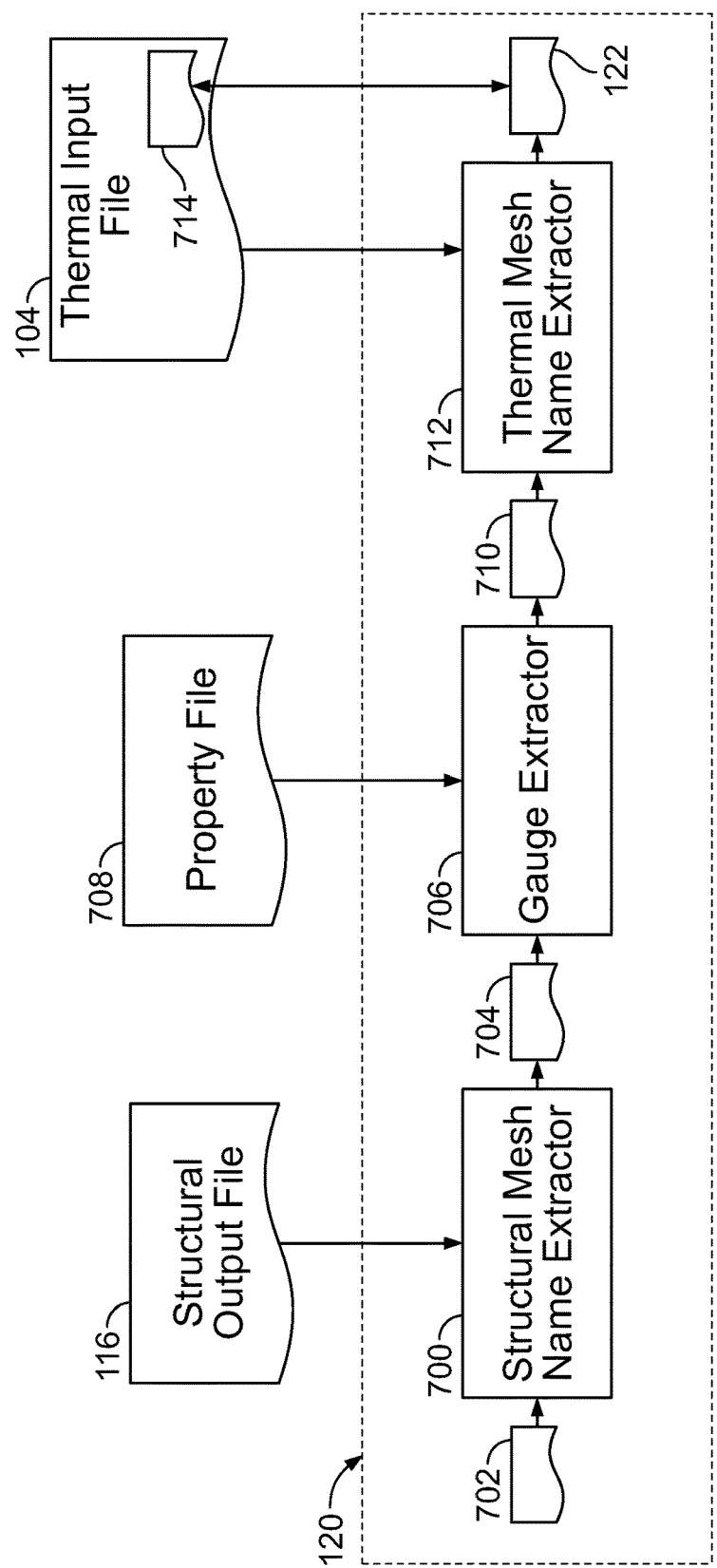
FIG. 7 is a block diagram of the example structural-to-thermal mapper of FIG. 1.

FIG. 7 is a more detailed block diagram of the example structural-to-thermal mapper 120. The structural-to-thermal mapper 120 includes a structural mesh name extractor 700, which extracts the property names from nodes nearest the reference points. The name extractor 700 opens the structural output file 116 (e.g., in Hypermesh) and reads locations of the reference points from a CSV file 702. An example of the CSV 702 file may include:

| Ref. Name | X | Y | Z |
|---|---|---|---|
| G1 | 1 | 2.5 | 0 |
| G2 | 4 | 2.5 | 0 |
| G3 | 8 | 2.5 | 0 |

The CSV file 702 includes a name for each of the reference points and the coordinates for each of the reference points. The structural mesh name extractor 700 creates a temporary or reference node at each location. For instance, a temporary or reference node may be created at a center of each of the zones 600, 602, 604 in the structural mesh at the coordinates of the reference points from the CSV file 702. As illustrated in FIG. 6, a first reference node 606 is created in the first zone 600 at the coordinates of the first reference point G1, a second reference node 608 is created in the second zone 602 at the coordinates of the second reference point G2, and a third reference node 610 is created in the third zone 600 at the coordinates of the third reference point G3. The structural mesh name extractor 700 finds the nearest nodes to each of the reference nodes 606, 608, 610 and extracts the property names for those nodes. For example, the nearest node to the first reference node 606 is node 612, the nearest node to the second reference node 608 is node 614, and the nearest node to the third reference node 610 is node 616. The structural mesh name extractor 700 updates the CSV file 702 with the property names to produce an updated or output CSV file 704. For example, the property name associated with the node 612 may be PSHELL1, the property name associated with the node 614 may be PSHELL2, and the property name associated with the node 616 may be PSHELL3. Therefore, an example of the CSV file 704 may include:

| Node Name | X | Y | Z | Structural Property Name |
|---|---|---|---|---|
| G1 | 1 | 2.5 | 0 | PSHELL1 |
| G2 | 4 | 2.5 | 0 | PSHELL2 |
| G3 | 8 | 2.5 | 0 | PSHELL3 |

As shown above, the CSV file 704 includes the coordinates of the references nodes 606, 608, 610 and the structural property names associated with nodes 612, 614, 616, which are the nodes closest to each of the reference nodes 606, 608, 610.

As illustrated in FIG. 7, the structural-to-thermal mapper 120 includes a gauge extractor 706, which receives the CSV file 704 (e.g., as an input file to the gauge extractor 706 and a property file 708 (e.g., which is a property file associated with the structural output file 116). The gauge extractor 706 opens the property file 708 (e.g., a .prop file) to extract the optimized gauges for the corresponding nodes. An example of the property file 708 may include:

```
$
$ ----------------------------------------------------------------
$ PROPERTIES AND MATERIALS AT ITERATION  2
$ ----------------------------------------------------------------
$
$HMNAME PROP              10"GAGE1" 4
$HWCOLOR PROP             10     9
PSHELL1       29    2     .1    2    1.0  2.8333333    0.0
$HMNAME PROP              11"GAGE2" 4
$HWCOLOR PROP             11    29
PSHELL2       30    2     .15   2    1.0  2.8333333    0.0
$HMNAME PROP              12"GAGE3" 4
$HWCOLOR PROP             12    37
PSHELL3       31    2     .2007 2    1.0  2.8333333    0.0
```

The gauge extractor 706 reads the property names from the property file 708, compares the property names with the names from the CSV file 704, extracts the optimized gauge sizes from the property file 708 and updates the CSV file 704 with the optimized gauge sizes to create an updated or output CSV file 710. For example, as shown in the property file 708 above, the optimized gauge size for PSHELL1 is 0.1 inches, the optimized gauge size for PSHELL2 is 0.15 inches and the optimized gauge size for PSHELL3 is 0.2007 inches. Therefore, an example of the CSV file 710 may include:

| Node Name | X | Y | Z | Structural Property Name | Structural Thickness |
|---|---|---|---|---|---|
| G1 | 1 | 2.5 | 0 | PSHELL1 | 0.1 |
| G2 | 3 | 2.5 | 0 | PSHELL2 | 0.15 |
| G3 | 5.5 | 2.5 | 0 | PSHELL3 | 0.2007 |

As shown above, the CSV file 710 includes the optimized gauge sizes associated with the nodes 612, 614, 616. The structural-to-thermal mapper 120 includes a thermal mesh name extractor 712. The thermal mesh name extractor 712 opens the thermal input file 104 (e.g., in Hypermesh) and reads the points from the CSV file 710 to create reference nodes in the thermal mesh 202 at the locations of the reference points. For example, as illustrated in FIG. 6, a first reference node 618 is created in the thermal mesh 200 at the coordinates the first reference point G1 in the structural mesh 202. A common or global coordinate system may be used, referenced from the bottom left corner point, for example. Likewise, a second reference node 620 is created in the thermal mesh 200 at the coordinates of the second reference point G2 in the structural mesh 202, and a third reference node 622 is created at the coordinates of the third reference point G3 in the structural mesh 202.

The thermal mesh name extractor 712 finds the nearest node to each of the reference nodes 618, 620, 622 in the thermal mesh 200. For example, node 624 is the closest node to the first reference node 618, node 626 is the closest node to the second reference node 620 and node 628 is the closest node to the third reference node 622. The property names and/or identification information for the nodes 624, 626, 628 are extracted and the CSV file 710 is updated with the corresponding names to produce the CSV file 122. For example, the thermal property name of the node 624 may be GAUGE1, referring to a first gauge size associated with the nodes of the first zone 600, the thermal property name for the node 626 may be GAUGE2, referring to a second gauge size associated with the nodes of the second zone 602, and thermal property name of the node 628 may be GUAGE3, referring to a third gauge size associated with the nodes of the third zone 604. Therefore, an example of the CSV file 122 may include:

| Node Name | X | Y | Z | Structural Property Name | Structural Thickness | Thermal Property Name | Thermal Thickness |
|---|---|---|---|---|---|---|---|
| G1 | 1 | 2.5 | 0 | PSHELL1 | 0.1 | GAUGE1 | 0.1 |
| G2 | 3 | 2.5 | 0 | PSHELL2 | 0.15 | GAUGE2 | 0.15 |
| G3 | 5.5 | 2.5 | 0 | PSHELL3 | 0.2007 | GAUGE3 | 0.2007 |

In the thermal input file 104, the nodes in the first zone 600 all have the property name GAUGE1. Therefore, all of the nodes in the first zone 600 in the thermal mesh 200 can be assigned the GAUGE1 thickness of 0.1 inches. Similarly, all of the nodes in the second zone 602 have the property name GAUGE2 and can be assigned the GAUGE2 thickness of 0.15 inches, and all of the nodes in the third zone 604 have the property name GAUGE3 and can be assigned the GAUGE3 thickness of 2.007 inches. Thus, the gauge sizes from the structural output file 116 can be mapped to the nodes of the thermal mesh 200 of the thermal input file 104.

In some examples, the structural-to-thermal mapper 120 creates a CC file 714 (e.g., ".cc") for the thermal input file 104 that sets the gauges associated with the thermal property names. An example CC file 714 includes:

Header Register Data
GAUGE1=0.1 $ Thickness in inches
GAUGE2=0.15 $ Thickness in inches
GAUGE3=0.2007 $ Thickness in inches Therefore, the nodes of the thermal mesh 200 having the thermal property name GAUGE1 are assigned a thickness value of 0.1 inches, the nodes of the thermal mesh 200 having the thermal property name GAUGE2 are assigned a thickness value of 0.15 inches, and the nodes of the thermal mesh 200 having the thermal property name GAUGE3 are assigned a thickness value of 0.2007 inches. Thus, whenever the gauge sizes are changed via a structural analysis, the gauges sizes are mapped to the nodes in the thermal mesh 200 of the thermal input file 104.

If the property names of the nodes in the structural mesh 202 are the same as the nodes in the thermal mesh 200, then the structural-to-thermal mapper 120 opens the property file 708, reads the property names from the property file 708, reads the optimized gauges for the property names, and creates the CC file 714 (e.g., ".cc") for the thermal analyzer 102 with property names and their corresponding gauges. For example, if the structural mesh 202 and the thermal mesh 200 use the property names THICK1, THICK2, THICK3, etc. to refer to the gauge sizes, the CC file 718 may include:

Header Register Data
THICK1=0.1 $ Thickness in inches
THICK2=0.15 $ Thickness in inches
THICK3=0.2007 $ Thickness in inches Referring to FIG. 1, the structural-to-thermal mapper 120 updates the thermal input file 104 with the gauge sizes, which is then used by the thermal analyzer 102 to perform a thermal analysis. With the updated gauges, the thermal analysis may be performed again. If none of the thermal constraints are violated, then the design variables or parameters (e.g., the gauges sizes and temperature constraints) of the component have been optimized. If not, the new thermal distribution information may then be sent back to the structural analyzer 106 where the structural analyzer 106 can perform the structural analysis again with the updated thermal distribution information. This cycle may be performed until the design variables converge, within the constraints, and the objectives are met. In the illustrated example, the optimization tool 118 monitors the results of the thermal analysis and the structural analysis to determine if the results meet the input criteria. The input criteria may include design variables, such as gauge sizes, material type, etc., constraints such as temperature margins, allowable temperatures, fatigue, etc. and objectives such as minimizing weight.

In the illustrated example, the thermal analysis was described as being performed first, and the structural analysis second, and so forth. However, in other examples, the structural analysis could be performed first, with initial temperatures at the nodes, and then the gauges could be sent to the thermal analyzer, and so further. Therefore, the cycle may start with either the thermal analysis or the structural analysis.

While an example manner of implementing the example system 100 and example structural-to-thermal mapper 120 is illustrated in FIGS. 1 and 7, one or more of the elements, processes and/or devices illustrated in FIGS. 1 and 7 may be combined, divided, re-arranged, omitted, eliminated and/or implemented in any other way. Further, the example thermal analyzer 102, the example thermal input file 104, the example structural analyzer 106, the example structural input file 108, the example thermal output file 110, the example thermal-to-structural mapper 112, the example file 114, the example structural output file 116, the example optimization tool 118, the example structural-to-thermal mapper 120, the example file 122, the example structural mesh name extractor 700, the example CSV file 702, the example CSV file 704, the example gauge extractor 706, the example property file 708, the example CSV file 710, the example thermal name extractor 712, the example file 714 and/or, more generally, the example system 100 and the example structural-to-thermal mapper 120 of FIGS. 1 and 7 may be implemented by hardware, software, firmware and/or any combination of hardware, software and/or firmware. Thus, for example, any of the example thermal analyzer 102, the example thermal input file 104, the example structural analyzer 106, the example structural input file 108, the example thermal output file 110, the example thermal-to-structural mapper 112, the example file 114, the example structural output file 116, the example optimization tool 118, the example structural-to-thermal mapper 120, the example file 122, the example structural mesh name extractor 700, the example CSV file 702, the example CSV file 704, the example gauge extractor 706, the example property file 708, the example CSV file 710, the example thermal name extractor 712, the example file 714 and/or, more generally, the example system 100 and the example structural-to-thermal mapper 120 of FIGS. 1 and 7 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, thermal analyzer 102, the example thermal input file 104, the example structural analyzer 106, the example structural input file 108, the example thermal output file 110, the example thermal-to-structural mapper 112, the example file 114, the example structural output file 116, the example optimization tool 118, the example structural-to-thermal mapper 120, the example file 122, the example structural mesh name extractor 700, the example CSV file 702, the example CSV file 704, the example gauge extractor 706, the example property file 708, the example CSV file 710, the example thermal name extractor 712, and/or the example file 714 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 100 and the example structural-to-thermal mapper 120 may include one or more elements, processes and/or devices in addition to, or instead of, those illustrated in FIGS. 1 and 7, and/or may include more than one of any or all of the illustrated elements, processes and devices.

Flowcharts representative of example methods for implementing the example system 100 of FIG. 1 and/or the example structural-to-thermal mapper 120 of FIG. 7 are shown in FIGS. 8, 9, 10 and 11. In these examples, the methods may be implemented using machine readable instructions that comprise a program for execution by a processor such as the processor 1212 shown in the example processor platform 1200 discussed below in connection with FIG. 12. The program may be embodied in software stored on a tangible computer readable storage medium such as a CD-ROM, a floppy disk, a hard drive, a digital versatile disk (DVD), a Blu-ray disk, or a memory associated with the processor 1212, but the entire program and/or parts thereof could alternatively be executed by a device other than the processor 1212 and/or embodied in firmware or dedicated hardware. Further, although the example program is described with reference to the flowcharts illustrated in FIGS. 8-11, many other methods of implementing the example system 100 and/or the example structural-to-thermal mapper 120 may alternatively be used. For example, the order of execution of the blocks may be changed, and/or some of the blocks described may be changed, eliminated, or combined.

As mentioned above, the example methods of FIGS. 8-11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example methods of FIGS. 8-11 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 8:
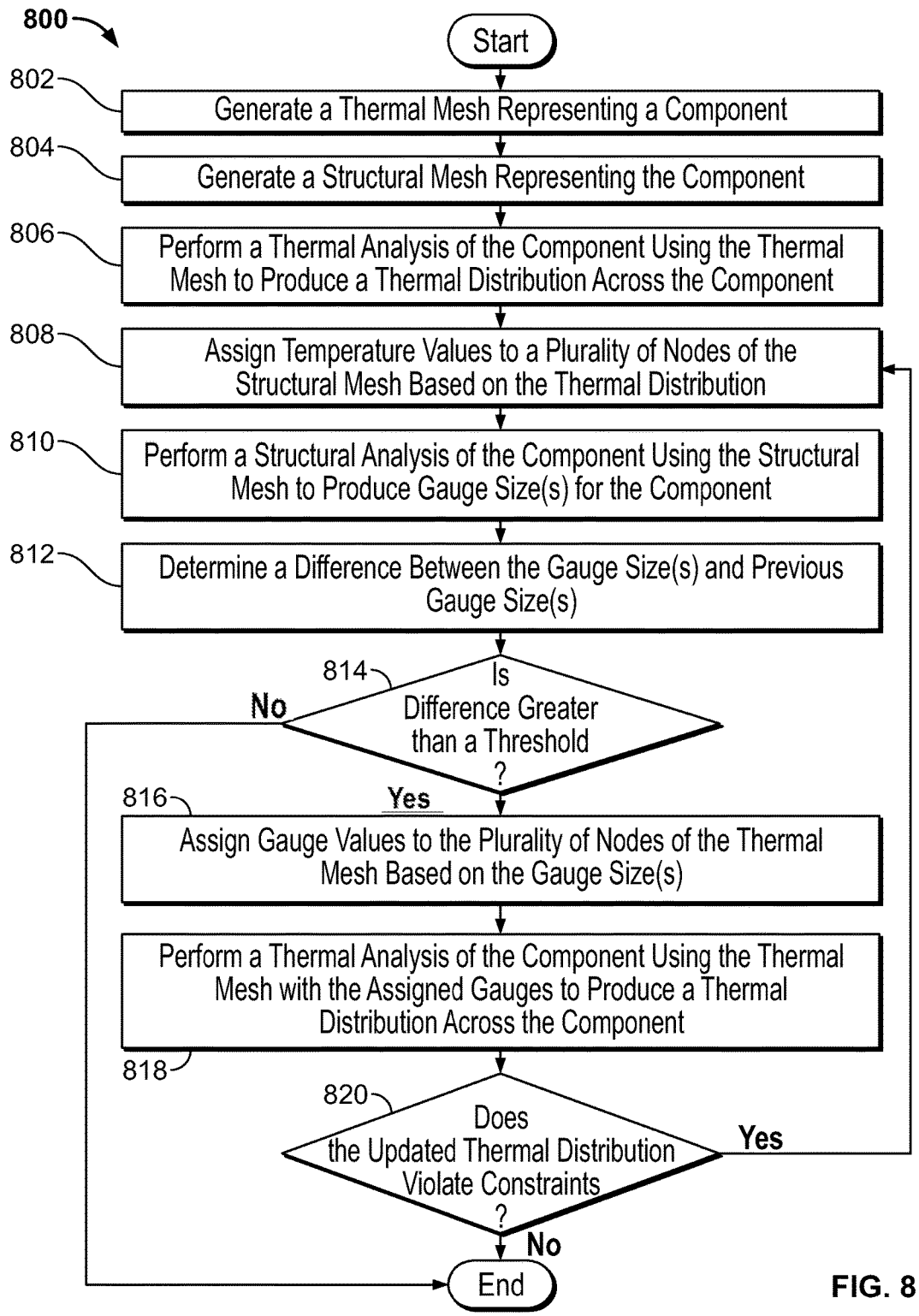
FIG. 8 is a flowchart representative of an example method of optimizing thermal and structural analyses that may be implemented by the example system of FIG. 1.

FIG. 8 illustrates a flowchart representative of an example method 800 to optimize thermal and structural analyses that may be implemented by the example system 100 of FIG. 1. The example method 800 includes generating a thermal mesh (e.g., a coarse mesh) representing a component (block 802). For example, in the system 100 of FIG. 1, the thermal analyzer 102 may generate or create a thermal mesh (e.g., the thermal mesh 200 of FIG. 2) representing a component. The coordinates of the nodes of the thermal mesh 200 and other associated information may be included in the thermal input file 104. The example method 800 includes generating a structural mesh (e.g., a fine mesh) representing the component (block 804). For example, in the system 100 of FIG. 1, the structural analyzer 106 may generate or create a structural mesh (e.g., the structural mesh 202 of FIG. 2) representing a component. The coordinates of the nodes of the structural mesh 202 and other associated information may be included in the structural input file 108. In some examples, the thermal mesh and the structural mesh often do not have overlapping nodes. For example, the thermal mesh may be coarser than the structural mesh.

The example method 800 includes performing a thermal analysis of the component using the thermal mesh to produce a thermal distribution (e.g., thermal distribution information) across the component (block 806). The analysis may be, for example, a finite element analysis (FEA), which is a technique used to find solutions to value problems by subdividing the whole into a plurality of nodes. For example, in the system 100 of FIG. 1, the thermal analyzer 102 performs a thermal analysis of the component using the thermal mesh 200 and produces thermal distribution information (e.g., the thermal distribution map 300 as illustrated in FIG. 3 and/or nodal temperatures of the thermal mesh 200 as illustrated in FIG. 4).

The example method 800 of FIG. 8 includes assigning temperature values to a plurality of nodes of the structural mesh based on the thermal distribution (block 808). As mentioned above, because the thermal mesh and the structural mesh are different, the coordinates of the nodes of the thermal mesh do not correspond to the nodes of the structural mesh. Therefore, the thermal distribution information is mapped (e.g., from the nodes of the thermal mesh) to the nodes of the structural mesh so that the information can be used in the structural analysis of the component. For example, the thermal-to-structural mapper 112 of the system 100 maps the thermal distribution information (e.g., from the thermal distribution map 300 and/or using the nodal temperatures of the thermal mesh 200) to the nodes of the structural mesh. In some examples, a mapping file (e.g., the file 114) is used to assign temperature values to the nodes of the structural mesh. An example method 900 of mapping thermal distribution information is disclosed in FIG. 9.

The example method 800 includes performing a structural analysis of the component using the structural mesh to produce one or more gauge size(s) (e.g., structural distribution information, optimal gauge sizes) for the component (block 810). For example, in the system 100 of FIG. 1, the structural analyzer 106 performs a structural analysis of the component using the structural mesh 202 and produces optimal gauge sizes for the component. The gauge sizes may be associated with the nodes of the structural mesh 202.

The example method 800 includes determining a difference between the gauge size(s) produced by the structural analysis and previous or initial gauge size(s) used when performing the thermal analysis (block 812). For example, in the system 100 of FIG. 1, the optimization tool 118 may determine if the calculated gauge sizes, as determined by the structural analyzer 106, are different from the gauge sizes initially used in the thermal analysis by the thermal analyzer 102. The example method 800 includes determining if the difference is greater than a threshold (block 814). The threshold may be a minimum amount of change in the gauge sizes, for example. For example, in the example system 100 of FIG. 1, the optimization tool 118 may determine if the gauge sizes have changed more than a threshold amount, and the thermal analysis may need to be performed again. If the gauge sizes are relatively close (e.g., less than a threshold) to the gauges sizes previously used, then the results of the thermal and structural analysis may be completed and the design variables optimized.

If the difference is greater than a threshold, the example method 800 includes assigning gauge value(s) to the plurality of nodes of the thermal mesh based on the gauge size(s) (block 816). For example, in the example system 100 of FIG. 1, the structural-to-thermal mapper 120 correlates the gauge information to the nodes of the thermal mesh. In some examples, a mapping file (e.g., the file 122) is used to assign gauge values to the nodes of the thermal mesh. An example method 1000 of mapping structural information is disclosed in FIG. 10.

The example method 800 of FIG. 8 includes performing a thermal analysis (e.g., a second or subsequent thermal analysis) on the component using the thermal mesh with the assigned or updated gauge sizes to produce a thermal distribution across the component (block 818). For example, in the example system 100 of FIG. 1, the thermal input file 104 includes the thermal mesh and the updated gauges for the nodes of the thermal mesh, which is then used when analyzing the component via the thermal analyzer 102. The example method 800 includes determining if the updated thermal distribution violates thermal constraints (block 820). If the updated thermal distribution does not violate the thermal constraints, the results of the thermal and structural analyses may be completed. Otherwise, the updated thermal distribution is mapped or assigned to the nodes of structural mesh so that the structural analysis can be performed again and verified (block 808). This cycle may continue until the thermal and structural constraints are met and the design variables of the component converge and, thus, are optimized. In some examples, multiple iterations are performed.

Figure 9:
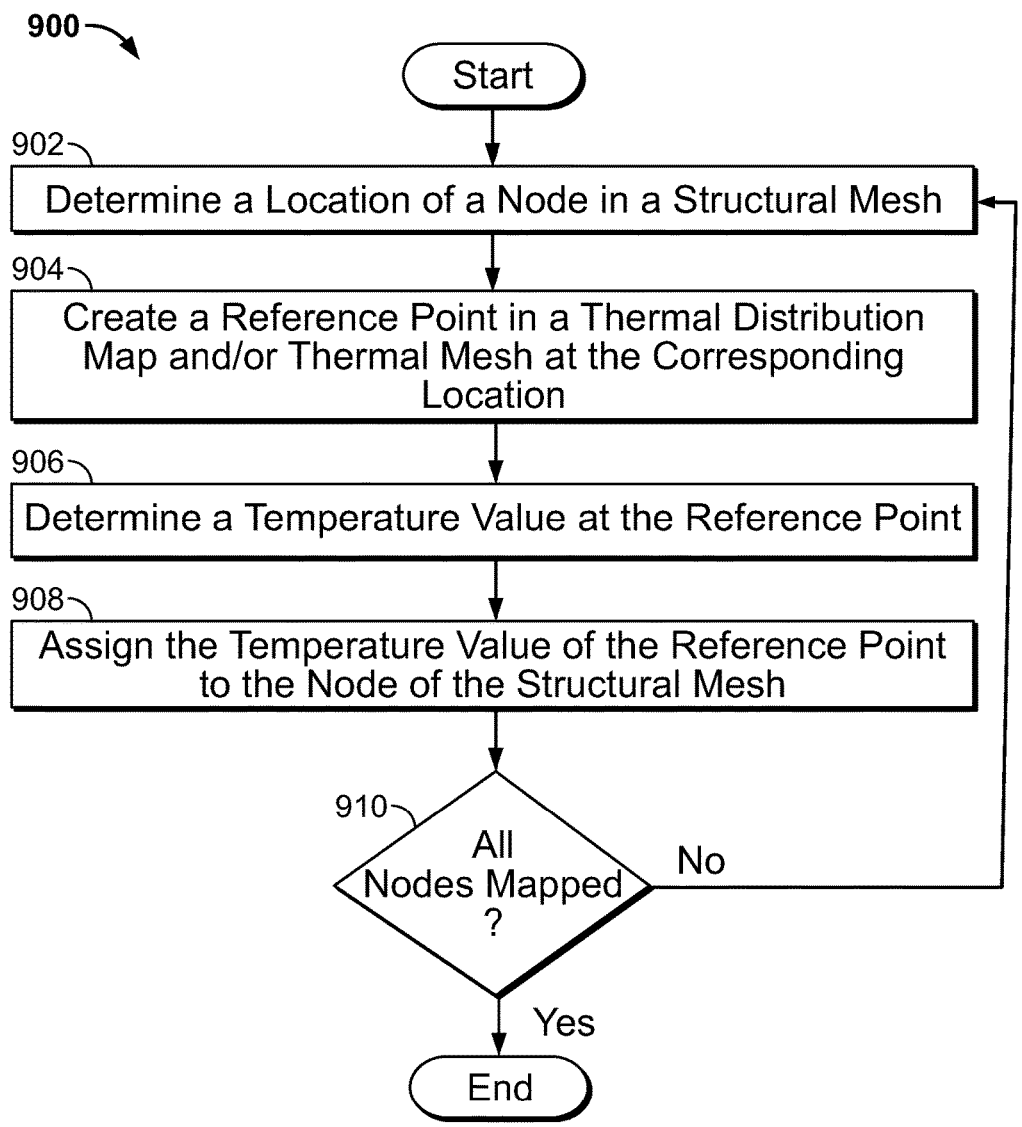
FIG. 9 is a flowchart representative of an example mapping technique to associate thermal distribution information from a thermal distribution map and/or from nodes of a thermal mesh to nodes of a structural mesh that may be implemented by the example system of FIG. 1.

FIG. 9 illustrates a flowchart representative of an example method 900 to associate or map thermal distribution information (e.g., nodal temperatures) from nodes of a thermal mesh or from a thermal distribution map to nodes of a structural mesh, and which may be implemented by the example system 100 of FIG. 1. As disclosed herein, the thermal analysis results in a thermal distribution, which may be represented by a thermal distribution map (e.g., the thermal distribution map 300 of FIG. 3) and/or by nodal temperatures of the thermal mesh (e.g., as illustrated in FIG. 4). The structural mesh and the thermal mesh may have different element sizes and, thus, the coordinates of nodes of the thermal mesh may not align with nodes of the structural mesh, and vice versa. The example method 900 includes determining a location (e.g., the coordinates) of a first node in a structural mesh (block 902). For example, as illustrated in FIG. 4, the thermal-to-structural mapper 112 (FIG. 1) determines a location of the node 400 in the structural mesh 202 based on a global coordinate system. The example 900 includes creating a reference point or node in the thermal distribution map and/or thermal mesh at the corresponding location (block 904). For example, as illustrated in FIG. 3, the reference point 402 is created in the thermal distribution map 300 at the coordinates of the node 400. Additionally or alternatively, the reference point 404 may be created in the thermal mesh 200, as illustrated in FIG. 4.

The example method 900 includes determining a temperature value at the reference point (block 906). For example, in FIG. 3, the temperature value at the reference point 402 may be determined based on where the reference point 402 is located in the thermal distribution map 300. Additionally or alternatively, with the reference point 404 in the thermal mesh 200 of FIG. 4, the temperature value at the reference point 404 may be calculated by integrating the thermal distribution information (e.g., nodal temperatures) of the thermal mesh 200 with respect to a scaling factor. In some examples, the temperature values of two or more nodes near the reference point 404 are integrated (e.g., via a derivative) to determine the temperature value at the reference point 404.

The example method 900 of FIG. 9 includes assigning or associating the temperature value of the reference point to the node of the structural mesh (block 908). For example, the thermal-to-structural mapper 112 may associate or assign the temperature value at the reference point 402 (FIG. 3) and/or reference point 404 (FIG. 4) to the node 400 in the structural mesh 202 (FIG. 4). The thermal-to-structural mapper 112 may create the file 114 (e.g., a TCL/tk scripting file) to associate the location and temperature of the reference point 402 and/or the reference point 404 to the node 400. The example method 900 includes determining if all of the nodes of the structural mesh have been mapped with thermal distribution information (e.g., assigned temperature values) (block 910). If not, the example method 900 includes determining a location of another node in the structural mesh (block 902), and the example method 900 repeats. This cycle may be repeated for each node of the structural mesh. Otherwise, the example method 900 may end. Therefore, the thermal distribution information of the thermal output file 110 can be mapped to the nodes of the structural mesh in the structural input file 108.

Figure 10:
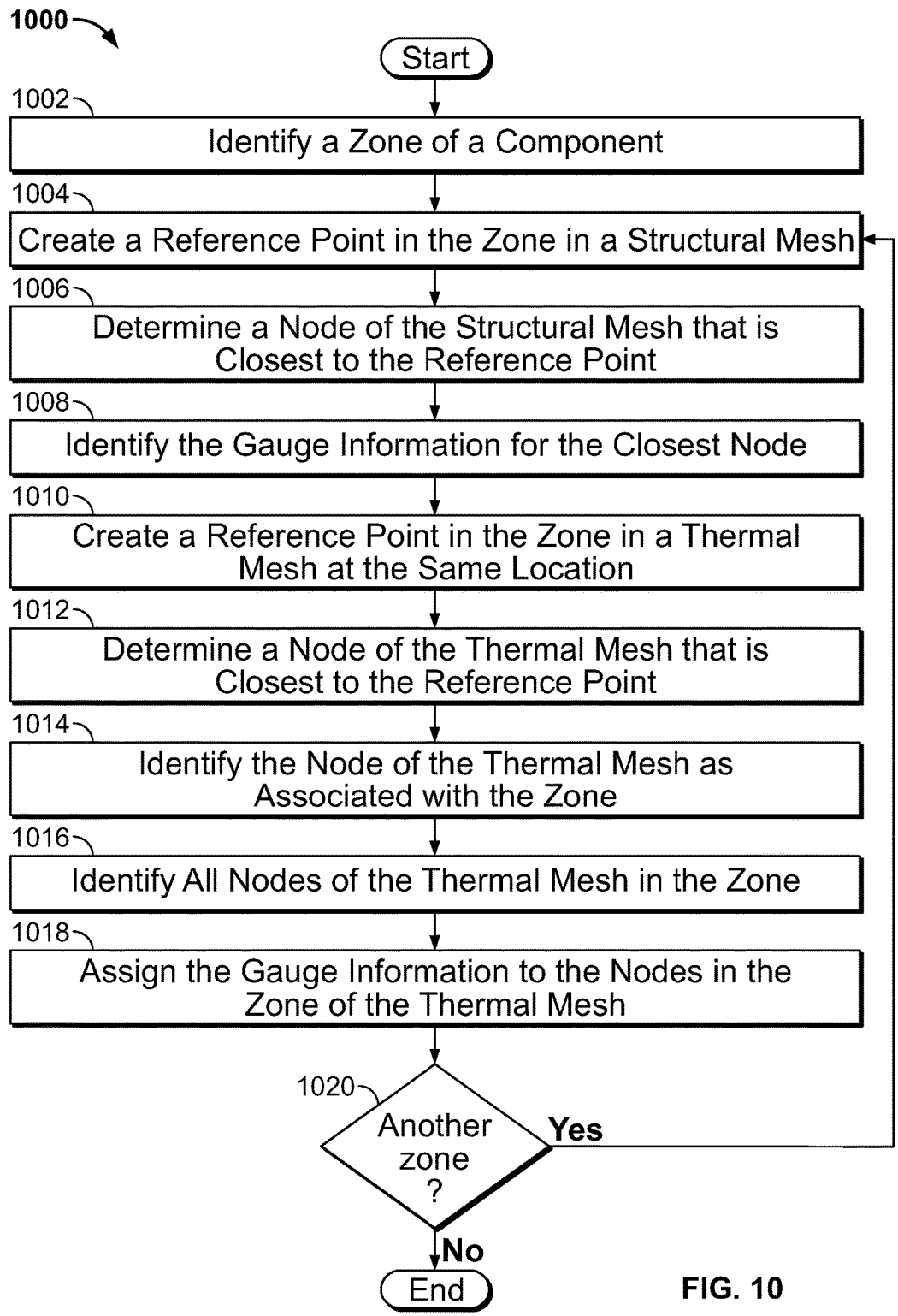
FIG. 10 is a flowchart representative of an example mapping technique to associate structural information, such as gauge sizes, from a structural mesh to nodes of a thermal mesh that may be implemented by the example system of FIG. 1.

FIG. 10 illustrates a flowchart representative of an example method 1000 to associate gauge information (e.g., gauge sizes) from nodes of a structural mesh to nodes of a thermal mesh, which may be implemented by the example system 100 of FIG. 1. The example method 1000 includes identifying a zone of a component (block 1002). As disclosed herein, a thermal mesh and a structural mesh may be generated for a component. The thermal mesh and the structural mesh may have different element sizes and, thus, the nodes of each may not be aligned. A common or global coordinate system can be used to define one or more zones of the component. The gauge size or thickness across the zone is consistent. In some examples, multiple zones are defined. For example, a first zone may correspond to a first section of the component having a first gauge size, a second zone may correspond to a second section of the component having a second gauge size, etc. For example, as illustrated in FIG. 6, the first zone 600, the second zone 602 and the third zone 604 are shown on across the structural mesh 202.

The example method 1000 includes creating a reference point in the zone in a structural mesh (block 1004). For example, as illustrated in FIG. 6, the structural-to-thermal mapper 120 (FIG. 1) creates the first reference node 606 for the first zone 600 based on the coordinates of the reference point G1. The example method 1000 includes determining a node of the structural mesh that is closest to the reference point (block 1006). For example, as illustrated in FIG. 6, the structural-to-thermal mapper 120 (FIG. 1) determines or identifies the node 612 of the structural mesh 202 as the closest node to the first reference node 606. The example method 1000 of FIG. 10 includes identifying the gauge information such as, the gauge size, for the node that is the closest (block 1008). For example, the structural-to-thermal mapper 120 (FIG. 1) may identify a gauge size associated with the node 612.

The example method 1000 includes creating a reference point in the zone in a thermal mesh as the same location (block 1010). For example, as illustrated in FIG. 6, the structural-to-thermal mapper 120 (FIG. 1) creates the first reference node 618 in the thermal mesh 200 at the same coordinates of the first reference node 606 in the structural mesh 202. The example method 1000 includes determining a node of the thermal mesh that is closest to the reference point (block 1012). For example, as illustrated in FIG. 6, the structural-to-thermal mapper 120 (FIG. 1) determines or identifies the node 624 of the thermal mesh 200 as the closest node to the first reference node 618.

The example method 1000 includes identifying the node of the thermal mesh as associated with the zone (block 1014). For example, the structural-to-thermal mapper 120 (FIG. 1) may identify the node 624 as being part of the first zone 600. The example method 1000 includes identifying all of the nodes of the thermal mesh in the zone (block 1016)

and assigning the gauge information to the nodes in the zone (block 1018). The example method 1000 includes determining if there is another zone (block 1020). If there is another zone, the gauge of the zone may be mapped to the corresponding nodes in the thermal mesh, as disclosed. Otherwise, the example method 1000 ends.

Figure 11:
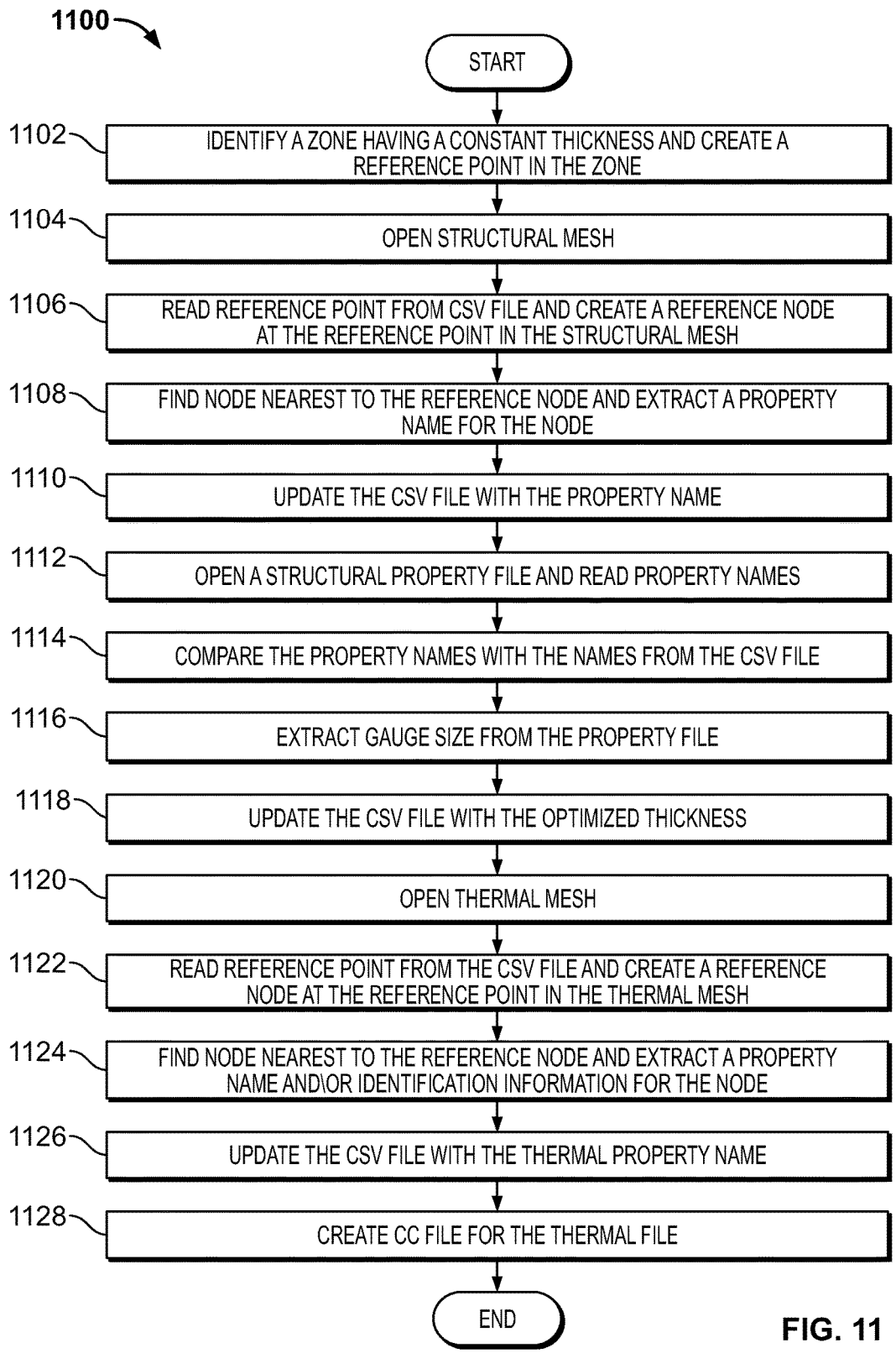
FIG. 11 is a flowchart representative of another example mapping technique to associate structural information, such as gauge sizes, from a structural mesh to nodes of a thermal mesh that may be implemented by the example system of FIG. 1.

FIG. 11 illustrates a flowchart representative of an example method 1100 to associate structural information, such as gauge sizes, from a structural mesh to nodes of a thermal mesh. The example method 1100 may be implemented by the example system 100 of FIG. 1. The example method 1100 may performed when the property names used in the thermal mesh and the structural mesh are different. The example method 1100 includes identifying a zone of a component having a constant thickness and creating a reference point in the zone (block 1102). For example, a zone may correspond to a first section of a modeled component having a thickness or gauge that is consistent across the entire section. The coordinates or location of the reference point is created in a CSV file. For example, as illustrated in FIG. 7, the CSV file 702 may include the coordinates of the reference points G1, G2 and G3. The example method 1100 includes opening a structural mesh (block 1104). For example, as illustrated in FIG. 7, the structural mesh name extractor may open the structural output file 116 (e.g., in Hypermesh). The example method 1100 includes reading the reference point from the CSV file and creating a reference node at the reference point in the structural mesh (block 1106). For example, as illustrated in FIG. 7, the structural mesh name extractor 700 may read the reference point(s) from the CSV file 702 and create reference node(s) in the structural mesh 202. As illustrated in FIG. 6, the first reference node 606 is created at the location of the reference point G1 from the CSV file 702.

The example method 1100 includes finding the node in the structural mesh that is nearest to the reference node and extracting a property name for that node (block 1108). For example, the structural mesh name extractor 700 may find the nodes 612, 614, 616, which are the nodes closest to the reference nodes 606, 608, 610, and extract the property names from the nodes 612, 614, 616. The example method 1100 includes updating the CSV file with the property name (block 1110). For example, the structural mesh name extractor 700 updates the CSV file 702 to create the CSV file 704 having the property names of the nodes 612, 614, 616.

The example method 1100 includes opening a structural property file and reading the property names (block 1112). For example, as illustrated in FIG. 7, the gauge extractor 706 opens the property file 708 and reads the property names from the property file 708. The example method includes comparing the property names with the property name in the CSV file (block 1114). For example, as illustrated in FIG. 7, the gauge extractor 706 may compare the property names in the property file 708 with the property names in the CSV file 704. The example method 1100 includes extracting a gauge size (e.g., an optimized thickness) from the property file (block 1116) and updating the CSV file with the gauge size (block 1118). For example, the gauge extractor 706 may extract the gauge size (e.g., 0.1 inches, 0.15 inches, etc.) from the property file 708 and update the CSV file 704 to create the updated CSV file 710.

The example method 1100 includes opening a thermal mesh (block 1120). For example, as illustrated in FIG. 7, the thermal mesh name extractor 712 opens the thermal input file 104 (e.g., in Hypermesh). The example method 1100 includes reading the reference point from the CSV file and creating a reference node at the reference point in the thermal mesh (block 1122). For example, the thermal mesh name extractor 712 may create the reference nodes 618, 620, 622 in the thermal mesh 200 that correspond to the reference points from the CSV file 710.

The example method 1100 includes finding the node nearest to the temporary node and extracting a property name and/or identification information for the node (block 1124). For example, the thermal mesh name extractor 712 find the node 624 is the node closest to the first reference node 618 in the thermal mesh 200 and may extract a property name and/or identification information associated with the node 624.

The example method 1100 includes updating the CSV file with the thermal property name (block 1126) and creating a CC file for the thermal input file (block 1128). As illustrated in FIG. 7, the thermal mesh name extractor 712 may update the CSV file 710 with the extracted property name to produce the file 122. In some examples, the structural-to-thermal mapper 120 creates the CC file 714, which may be implemented as header register information, to assign the gauge size to the property name in the thermal input file 104.

Figure 12:
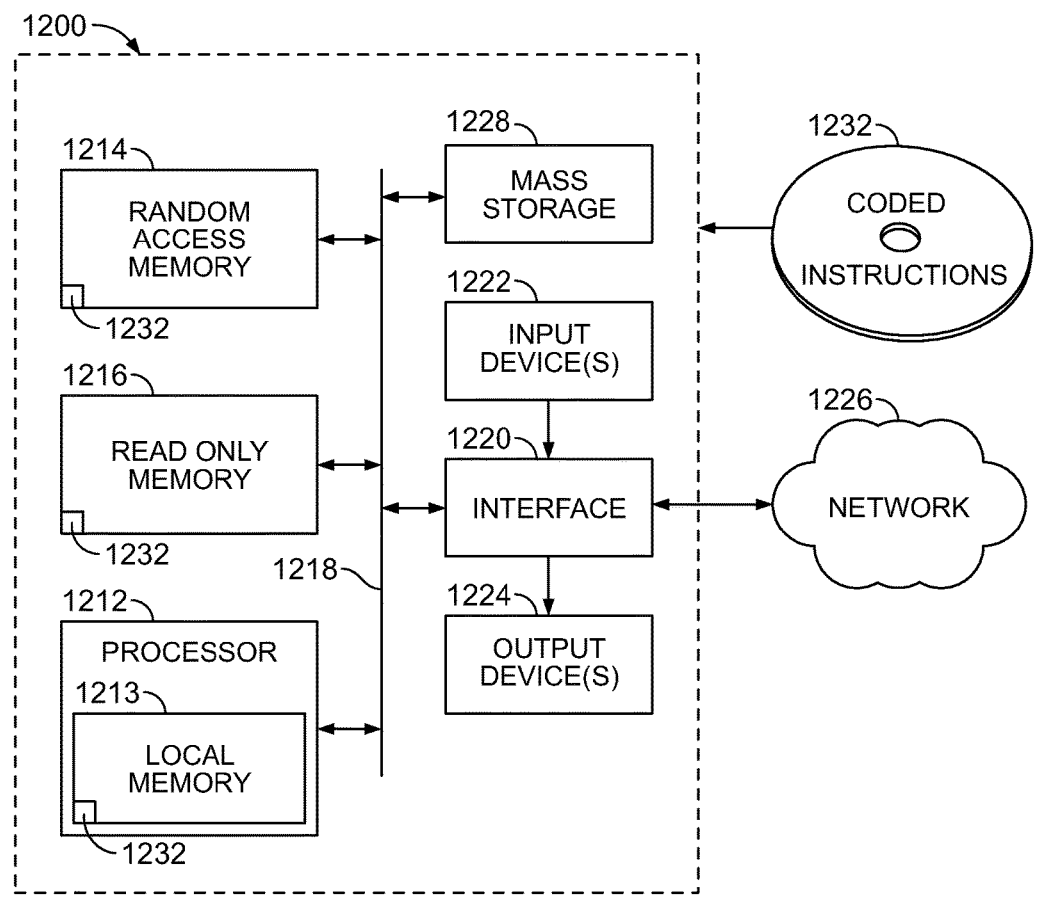
FIG. 12 is a block diagram of an example processor platform that may be used to implement the methods and apparatus described herein.

FIG. 12 is a block diagram of an example processor platform 1200 capable of executing the instructions to implement the methods of FIGS. 8-11 and to implement the example system 100 of FIG. 1. The processor platform 1200 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, or any other type of computing device.

The processor platform 1200 of the illustrated example includes a processor 1212. The processor 1212 of the illustrated example is hardware. For example, the processor 1212 can be implemented by one or more integrated circuits, logic circuits, microprocessors or controllers from any desired family or manufacturer.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), and/or a PCI express interface.

In the illustrated example, one or more input devices 1222 are connected to the interface circuit 1220. The input device(s) 1222 permit(s) a user to enter data and commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1220 of the illustrated example, thus, typically includes a graphics driver card, a graphics driver chip or a graphics driver processor.

The interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile disk (DVD) drives.

Coded instructions 1232 to implement the methods 800, 900, 1000, 1100 of FIGS. 8-11 may be stored in the mass storage device 1228, in the volatile memory 1214, in the non-volatile memory 1216, and/or on a removable tangible computer readable storage medium such as a CD or DVD.

From the foregoing, it will be appreciated that the above disclosed systems and methods integrate thermal and structural analyses to more efficiently optimize a design of a component. The example systems and methods may be used to map thermal distribution information to the nodes of a structural mesh and/or to map structural information to the nodes of a thermal mesh. As a result, the thermal and structural analyses can be performed more quickly, thereby producing a result in a much faster time than known systems.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method comprising:
   performing, via a thermal analyzer, a thermal analysis of a component for an aircraft using a first mesh in a thermal input file representing the component to produce a thermal distribution across the component, the first mesh having first nodes spaced apart based on a first node spacing size, wherein the thermal analysis produces a thermal output file containing the thermal distribution including first temperature values at the first nodes of the first mesh;
   generating, via a first mapper, a first mapping file that assigns second temperature values to second nodes of a second mesh in a structural input file representing the component based on the first temperature values from the first nodes in the thermal output file, the second nodes spaced apart based on a second node spacing size different than the first node spacing size;
   performing, via a structural analyzer, a structural analysis of the component using the second mesh in the structural input file with the second temperature values to determine optimal gauge values for the component, wherein the structural analysis produces a structural output file containing the optimal gauge values at the second nodes of the second mesh;
   generating, via a second mapper, a second mapping file that assigns gauge values to the first nodes of the first mesh in the thermal input file based on the optimal gauge values from the second nodes in the structural output file, wherein generating the second mapping file includes:
   identifying a first zone in the first mesh and a second zone in the second mesh, the first zone and the second zone corresponding to the same area of the component
   determining a first optimal gauge value in the second zone; and
   assigning the first optimal gauge value to the first nodes of the first mesh located in the first zone;
   iteratively performing the thermal analysis and the structural analysis in an alternating sequence until thermal and structural constraints are met, wherein, each time the thermal analysis is to be performed, the second mapping file is used to update the gauge values assigned to the first nodes in the thermal input file based on the optimal gauge values from the second nodes in the structural output file produced during a preceding structural analysis, and, each time the structural analysis is to be performed, the first mapping file is used to update the second temperature values assigned to the second nodes in the structural input file based on the first temperature values from the first nodes in the thermal output file produced during a proceeding thermal analysis; and
   in response to determining the thermal and structural constraints are met, outputting the optimal gauge values from the structural output file to be used to construct the component for the aircraft.

2. The method of claim 1, wherein the second node spacing size is smaller than the first node spacing size.

3. The method of claim 1, wherein generating the first mapping file includes:
   determining a coordinate of a node of the second nodes in the second mesh using a global coordinate system;
   creating a reference point at the coordinate in the thermal distribution using the global coordinate system;
   determining a temperature value at the reference point; and
   assigning the temperature value at the reference point to the node of the second nodes in the second mesh, the temperature value being one of the second temperature values assigned to one of the second nodes.

4. The method of claim 3, wherein determining the temperature value at the reference point includes integrating temperature values at two of the first nodes near the reference point.

5. The method of claim 1, wherein the thermal distribution is a map having one or more thermal boundaries.

6. The method of claim 1 further including determining a difference between the optimal gauge values and previous gauge values.

7. The method of claim 6, wherein, if the difference is greater than a threshold, the method includes performing, via the thermal analyzer, the thermal analysis on the first mesh a second time with the assigned gauge values to produce a second thermal distribution.

8. The method of claim 1, wherein the first mapping file is different than the second mapping file.

9. The method of claim 1, wherein determining the first optimal gauge value in the second zone includes:
   creating a reference point in the second zone of the second mesh;

identifying a node of the second nodes closest to the reference point; and determining an optimal gauge value of the node closest to the reference point.

10. An apparatus comprising:

a thermal analyzer to perform a thermal analysis of a component for an aircraft using a first mesh in a thermal input file representing the component to produce a thermal distribution across the component, the first mesh having first nodes spaced apart based on a first node spacing size, wherein the thermal analysis produces a thermal output file containing the thermal distribution including first temperature values at the first nodes of the first mesh;

a first mapper to generate a first mapping file that assigns second temperature values to second nodes of a second mesh in a structural input file representing the component based on the first temperature values from the first nodes in the thermal output file, the second nodes based on a second node spacing size different than the first node spacing size;

a structural analyzer to perform a structural analysis using the second mesh in the structural input file with the second temperature values to determine optimal gauge values for the component, wherein the structural analysis produces a structural output file containing the optimal gauge values at the second nodes of the second mesh;

a second mapper to generate a second mapping file that assigns gauge values to the first nodes of the first mesh in the thermal input file based on the optimal gauge values from the second nodes in the structural output file, wherein the second mapper is to generate the second mapping file by identifying a first zone in the first mesh and a second zone in the second mesh, the first zone and the second zone corresponding to the same area of the component, determining a first optimal gauge value in the second zone, and assigning the first optimal gauge value to the first nodes of the first mesh located in the first zone, wherein the thermal analyzer and the structural analyzer are to iteratively perform the thermal analysis and the structural analysis, respectively, in an alternating sequence until thermal and structural constraints are met, wherein, each time the thermal analysis is to be performed, the second mapping file is used to update the gauge values assigned to the first nodes in the thermal input file based on the optimal gauge values from the second nodes in the structural output file produced during a preceding structural analysis, and, each time the structural analysis is to be performed, the first mapping file is used to update the second temperature values assigned to the second nodes in the structural input file based on the first temperature values from the first nodes in the thermal output file produced during a proceeding thermal analysis; and an optimization tool to determine when the thermal and structural constraints are met and output the optimal gauge values from the structural output file to be used to construct the component for the aircraft.

11. The apparatus of claim 10, wherein the first mapping file maps a location of a first node of the second nodes with a reference point at a same location in the thermal distribution.

12. The apparatus of claim 10, wherein the first mapping file is a tool command language scripting file.

13. The apparatus of claim 12, wherein the second mapping file is a comma-separated values file.

14. A tangible computer readable storage medium comprising instructions that, when executed, cause a machine to at least:

generate a first mesh representing a component for an aircraft, the first mesh stored as a thermal input file, the first mesh having first nodes;

generate a second mesh representing the component, the second mesh stored as a structural input file, the second mesh having second nodes, a portion of the second nodes corresponding to different coordinates of the component than the first nodes;

perform a thermal analysis of the component using the first mesh in the thermal input file to produce a thermal distribution across the component, wherein the thermal analysis produces a thermal output file containing the thermal distribution including first temperature values for the first nodes of the first mesh;

assign, via a first mapping file, second temperature values to the second nodes of the second mesh in the structural input file based on the first temperature values from the first nodes in the thermal output file;

perform a structural analysis on the second mesh in the structural input file with the second temperature values to produce optimal gauge values for the component, wherein the structural analysis produces a structural output file containing the optimal gauge values at the second nodes of the second mesh;

assign, via a second mapping file, gauge values to the first nodes of the first mesh in the thermal input file based on the optimal gauge values from the second nodes in the structural output file, wherein assigning the gauge values to the first nodes includes:

identifying a first zone in the first mesh and a second zone in the second mesh, the first zone and the second zone corresponding to the same area of the component;

determining a first optimal gauge value in the second zone; and assigning the first optimal gauge value to the first nodes of the first mesh located in the first zone;

iteratively perform the thermal analysis and the structural analysis in an alternating sequence until thermal and structural constraints are met, wherein, each time the thermal analysis is to be performed, the second mapping file is used to update the gauge values assigned to the first nodes in the thermal input file based on the optimal gauge values from the second nodes in the structural output file produced during a preceding structural analysis, and, each time the structural analysis is to be performed, the first mapping file is used to update the second temperature values assigned to the second nodes in the structural input file based on the first temperature values from the first nodes in the thermal output file produced during a proceeding thermal analysis; and in response to determining the thermal and structural constraints are met, output the optimal gauge values from the structural output file to be used to construct the component for the aircraft.

15. The tangible computer readable storage medium of claim 14, wherein the instructions, when executed, cause the machine to determine the first optimal gauge value in the second zone by creating a reference point in the second zone of the second mesh and identifying an optimal gauge value of a closest one of the second nodes to the reference point.

16. The tangible computer readable storage medium of claim 15, wherein to identify the optimal gauge value of the closest node, the instructions, when executed, cause the machine to extract a property name associated with the closest node.

17. The tangible computer readable storage medium of claim 14, wherein to assign the second temperature values to the second nodes, the instructions, when executed, cause the machine to:
  determine a coordinate of a node of the second nodes in the second mesh using a global coordinate system;
  create a reference point at the coordinate in the thermal distribution using the global coordinate system;
  determine a temperature value at the reference point; and
  assign the temperature value at the reference point to the node of the second nodes in the second mesh, the temperature value being one of the second temperature values assigned to one of the second nodes.

\* \* \* \* \*